United States Patent [19]

Shelanski

[11] Patent Number: 4,838,284
[45] Date of Patent: Jun. 13, 1989

[54] METHOD OF USING A DERMATOME

[76] Inventor: Morris V. Shelanski, 431 Wister Rd., Wynnewood, Pa. 19096

[21] Appl. No.: 214,746

[22] Filed: Jul. 5, 1988

Related U.S. Application Data

[62] Division of Ser. No. 941,157, Dec. 12, 1986, Pat. No. 4,754,756.

[51] Int. Cl.⁴ .................................... A61B 17/322
[52] U.S. Cl. ........................... 128/898; 128/305.5
[58] Field of Search .............. 128/305.5, 314, 305, 128/898

[56]  References Cited

U.S. PATENT DOCUMENTS

| 1,594,613 | 8/1926 | Hagen. | |
|---|---|---|---|
| 1,786,246 | 11/1929 | Blair. | |
| 2,442,435 | 6/1948 | Reese. | |
| 2,721,555 | 10/1955 | Jenney. | |
| 3,037,509 | 6/1962 | Schutz. | |
| 3,364,920 | 1/1968 | Ross. | |
| 3,476,112 | 12/1969 | Elstein. | |
| 3,515,128 | 6/1970 | McEvoy | 128/305 X |
| 3,670,734 | 6/1972 | Hardy, Jr.. | |
| 3,820,543 | 6/1974 | Vanjushin et al.. | |
| 4,064,871 | 12/1977 | Reno | 128/314 X |
| 4,098,278 | 7/1978 | Schwartz. | |
| 4,438,770 | 3/1984 | Unger et al. | 128/314 X |

Primary Examiner—Michael H. Thaler
Attorney, Agent, or Firm—Steele, Gould & Fried

[57]  ABSTRACT

A dermatome is disclosed which includes a heavy metallic base, a hollow stem vertically supported upon the base, a blade carrying crosshead horizontally reciprocal within the base, a vertically movable plunger assembly adjustably secured within the stem and a bottom plate bottomly secured to the base below the reciprocating blade. The plunger assembly bottomly carries a replaceable pin and the bottom plate is provided with a cooperating operation to receive the pin therethrough. An operating lever pivotally secures to a yoke that is affixed to the stem and is used to urge the crosshead to an initial, cocked position. A safety pin is adjustably positioned in the yoke to prevent firing of the crosshead without first depressing the safety pin. In use, the crosshead is cocked and the plunger assembly pin is lowered through the opening to adhere to a skin specimen. Upon raising the plunger assembly, the skin specimen is drawn upwardly through the plate opening and above the plane of travel of the crosshead blade. Release of the safety pin and movement of the operating lever allows the crosshead to move to its final position, thereby severing the skin specimen with the blade.

4 Claims, 4 Drawing Sheets

METHOD OF USING A DERMATOME

This is a division, of application Ser. No. 941,157 filed Dec. 12, 1986, now U.S. Pat. No. ∝,754,756.

BACKGROUND OF THE INVENTION

1. Field of the Invention:

The present invention relates generally to surgical apparatus relating to severing specimens of skin, and more particularly, is directed to a dermatome capable of accurately reproducing the area and depth of cut of a series of specimen wounds.

2. Discussion of the Prior Art:

Numerous instruments have been developed by prior workers in the art for removing portions of the epidermis for skin grafts and other purposes. Such specialized instruments are generally referred to as dermatomes and these instruments have found considerable acceptance for the special purposes for which they have been employed.

The prior art types of dermatomes generally emplot a sharp cutting implement or blade which is adapted to slice through the epidermis to produce acceptable specimens for skin transplant and other purposes. In one widely accepted application, skin transplants of various widths are utilized for plastic surgery purposes during the treatment of large burn areas. The prior art dermatomes that have been developed for this purpose usually employ some type of means for adjusting the thickness of the transplant being cut away and for limiting the thickness of the cut.

Some of the dermatomes that have been developed to date for skin grafting and other purposes are quite complicated in construction and have required considerable training and practice prior to use. While such devices had to be ralatively sensitive in operation and precise in function for the intended purposes, the dermatomes that have heretofore been designed and manufactured have generally proved to be incapable of accurately reproducing a plurality of predetermined, similar wounds having substantially identical areas of cut and similar depth of cut. Additionally, the very nature of the operation of dermatomes has rendered their use considerably uncomfortable for the patient and the process of removing portions of the epidermis for skin grafting could be accompanied with a great deal of pain, unless some suitable means for anesthetizing the site could be employed. In many instances, a local anesthetic could not be employed because the injection of the anesthetics would have a tendency to distort the site and thereby inherently interfere with the accuracy or precision of the cut.

So far as is known to the present applicant, none of the prior art types of dermatomes have been particularly designed to achieve relatively uniform, reproducible wounds and specimens of skin by precisely controlling the area and the depth of cut.

SUMMARY OF THE INVENTION

The present invention relates generally to the field of surgical apparatus, and more particularly, is directed to a dermatome designed for painless operation wherein wounds can be standardized by accurately reproducing the area and depth of cut.

The dermatome of the present invention comprises generally an ajustable plunger with precise depth adjustment means which is securely supported upon a sturdy base for positioning over a predetermined area of the skin surface. By adhering a predetermined area of skin to the bottom of the plunger, the predetermined skin area can be elevated and stretched until the specimen to be taken is drawn into the path of cutting blade. A spring urged crosshead is reciprocal within the base below the plunger and is designed to quickly thrust a sharp blade, which may be a razor blade, beneath the plunger for speedy, skin severing purposes. Due to the speed of operation of the crosshead (and consequently the blade), a sample of the skin can be instantaneously cut in painless manner without the requirement for any type of anesthetic.

Accordingly, when the dermatome of the present invention is to be used to provide a plurality of standardized wounds for test purposes, the subjects employed for this purpose can be more readily recruited in view of the speedy and painless nature of the operations.

A lever which is a pivotal relative to the body is employed to urge the crosshead to its initial position against the bias of the crosshead springs. A crosshead mounted detent is cooperatively employed with an engaging toe extending from the lever to facilitate the cocking and subsequent release or firing of the crosshead for skin cutting purposes.

A safety or pin catch is operatively associated with the lever to prevent unwanted or unintentional firing of the crosshead. In order to operate the crosshead in its skin cutting mode, two conscious and simultaneous efforts on the part of the operator must be made, namely, both pressing the safety catch end knob and simultaneously squeezing the operating lever until the crosshead is released by pivoting the lever toe clear of the crosshead detent. In the event that either the squeezing of the lever or the pressing of the safety catch is omitted, the dermatome of the present invention will not and cannot function.

In the preferred embodiment, the bottom of the plunger is provided with a replaceable plunger pin whereby the size and shape of the skin sample taken can be easily varied, simply by replacing the plunger pin with another pin of different size or configuration. A bottom plate bottomly covers the body of the dermatome and the crosshead is reciprocal above the bottom plate. This plate is provided with an opening in vertical registry below the plunger pin. The bottom plate opening is particularly designed as to size and configuration complementary to the size and configuration of the plunger pin that had been selected to perform a particular operation or series of operations. The bottom plate is provided with an indented recess about the periphery of the hole or opening to allow a greater area of skin to contribute to the elasticity necessary for displacement of the sking upwardly into the bottom plate opening. In this manner, the required uniformity of cut can more readily be accomplished without inaccuracies being introduced due to the inelasticity of skin being sampled.

It is an important feature of this invention that the dematome has been particularly designed to be easily adoptable for multi-use purpose. The blade, the skin contacting pin and the bottom plate have been arranged for speedy removal and replacement and thus can be readily interchanged, sterilized, or replaced as necessary to meet the demands of any particular procedure or series of procedures.

A micrometer adjustment is built into the plunger mechanism so that the precise depth of cut can be rapidly arranged by adjusting the vertical position of the bottom of the plunger pin relative to the reciprocating razor blade as it is carried by the crosshead.

Preferably, a commercial type of flat razor blade, for example the flat blade employed in the "ATRA" razor system as manufactured and sold by Gillette Corporation can be mounted in the crosshead for specimen cutting purposes. The blade is mounted in an easily releasable manner whereby the blade can be readily removed for sterilization or replacement purposes. In the preferred embodiment, the cutting edge of the blade is arranged in angular relationship to the path of travel of the crosshead to facilitate the taking of specimens of predetermined shape and depth without the patient experiencing any inconvenience such as pain or other discomfort.

It is therefore an object of the present invention to provide an improved dermatome of the type set forth.

It is another object of the present invention to provide a novel dermatome comprising a body, a plunger vertically mounted on the body, the plunger being provided with vertical height adjusting means, a spring biased crosshead reciprocal within the body from an initial position out of registry with the plunger to a final position in registry below the plunger, a blade carried in the crosshead in angular relationship to the path of travel of the crosshead and lever means to urge the crosshead to its initial position against the bias of the crosshead springs, the lever means contorlling the release of the crosshead to its final position to sever a skin specimen of predetermined area and depth.

It is another object of the present invention to provide a novel dermatome comprising horizontal body means, a crosshead means horizontally reciprocal within the body means, the crosshead means carrying a blade means in angular relationship to the direction of crosshead travel, adjustable plunger means vertically carried by the body above the crosshead means, lever means to move the crosshead means to an initial, cocked position, safety catch means in engagement with the lever means to prevent unintentional firing of the crosshead and bottom plate means including an opening in registry below the plunger to facilitate the presentation of standardized samples of skin within the dermatome for severing by the blade means upon function of the crosshead means.

It is another object of the present invention to provide a novel dermatome that comprises a relatively few parts that require sterilization.

It is another object of the present invention to provide a novel dermatome that is easily adaptable for multiple use and which features a blade, a skin contacting pin and a bottom plate that are all easily removable for sterilization and/or replacement purposes.

It is another object of the present invention to provide a novel dermatome that is rugged in construction, precise in adjustment and trouble free when in use.

Other objects and a fuller understanding of the invention will be had by referring to the following description and claims of a preferred embodiment, taken in conjunction with the accompanying drawings, wherein like reference characters refer to similar parts throughout the several views in which:

DESCRIPTION OF THE PREFERRED EMBODIMENT OF THE INVENTION

Although specific terms are used in the following description for the sake of clarity, these terms are intended to refer only to the particular structure of the invention selected for illustration in the the drawings, and are not intended to define or limit the scope of the invention.

Figure 1:
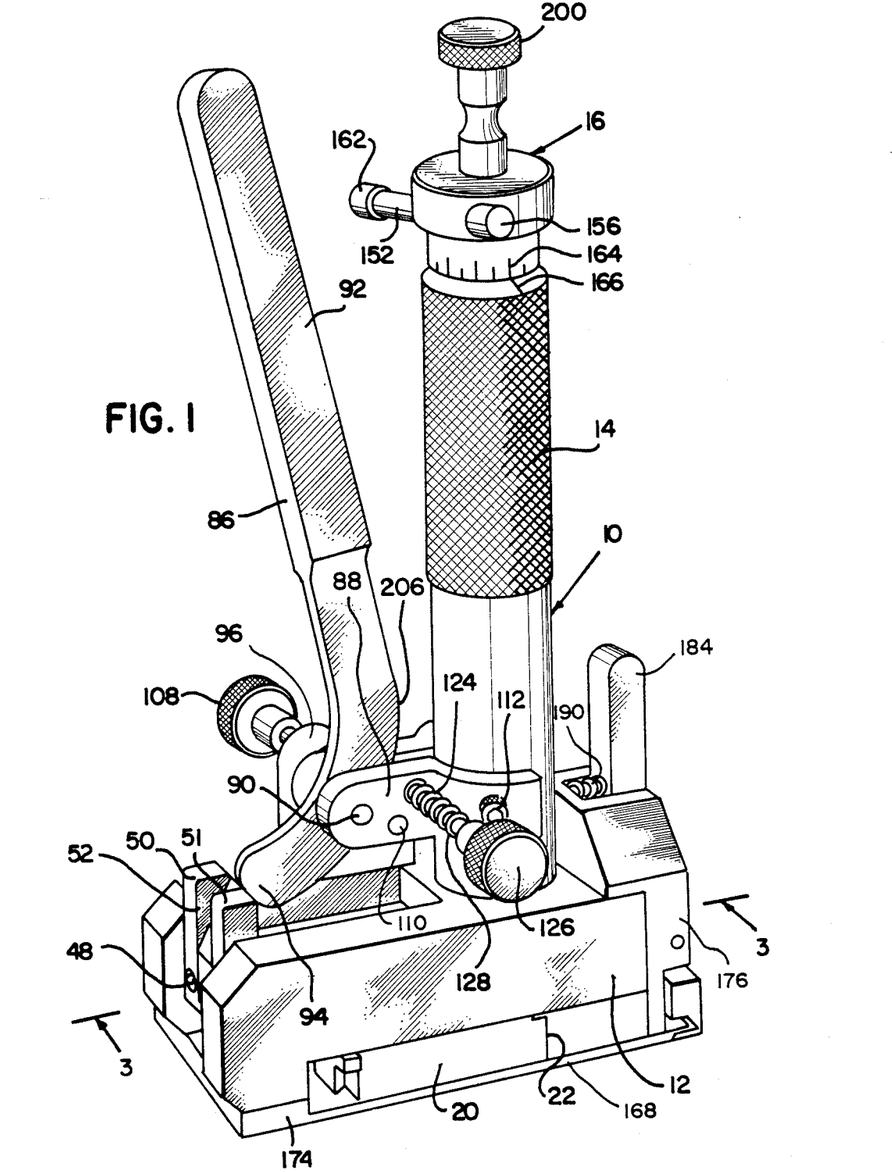
FIG. 1 is a perspective view showing the dermatome of the present invention ready for use.
Figure 2:
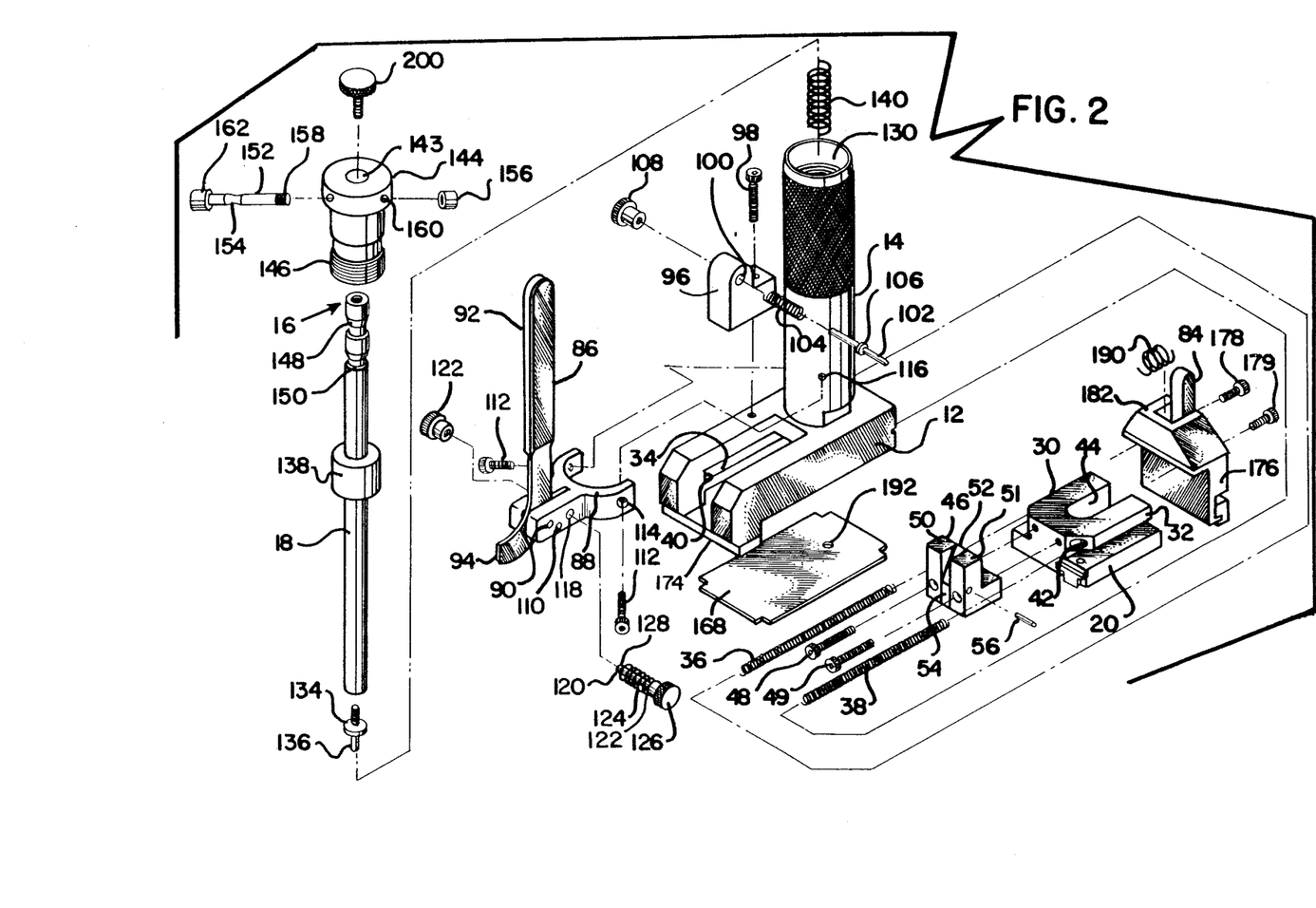
FIG. 2 is an exploded, perspective view of the dermatome of FIG. 1, on reduced scale.

Referring now to the drawings, there is shown in FIGS. 1 and 2 a dermatome 10 which comprises generally a heavy metal base or bottom 12 which is positioned in generally, horizontal orientation and to which is affixed a vertical, generally hollow barred or stem 14. A pluger assembly 16 is mounted within the barrel 14 in a manner to permit an elongated, vertical plunger 18 to be reciprocated from a lower, initial position as illustrated in FIG. 5 to an upper, final position as illustrated in FIGS. 3 and 7 for skin movement purposes through the bottom plate opening 192 in the manner hereinafter more fully set forth.

Figures 3, 4:
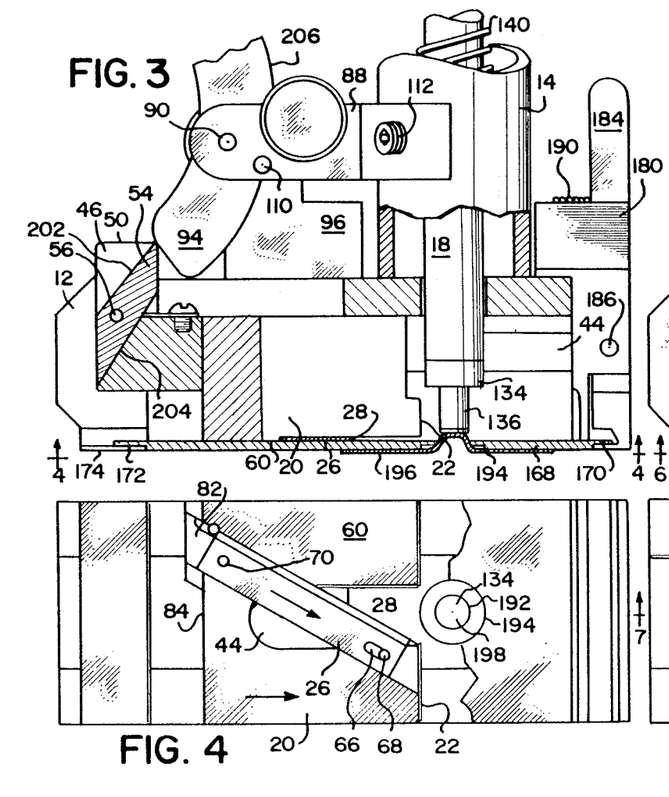
FIG. 3 is an elarged, partial, side elevational view taken along line 3—3 on FIG. 1, looking in the direction of the arrows, partially broken away to expose interior construction details, and showing the crosshead in its initial or cocked position.
FIG. 4 is a bottom plan view of the dermatome, looking from line 4—4 on FIG. 3, and partly broken away to expose interior construction details.
Figure 5:
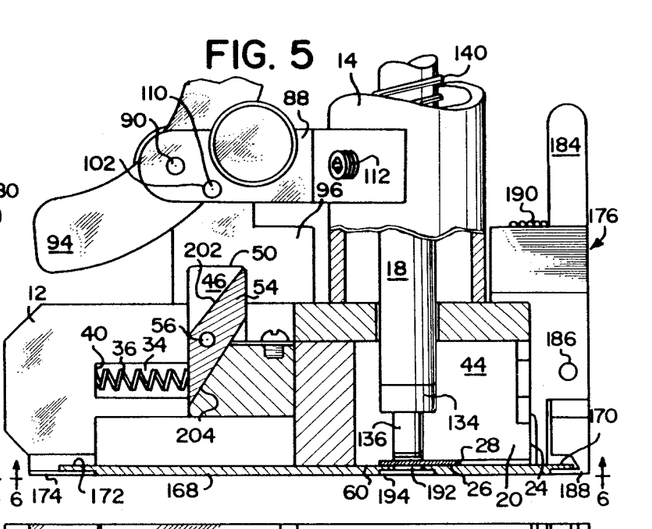
FIG. 5 is an enlarged, partial, side elevational view similar to FIG. 3, showing the crosshead in its fired or final position.
Figures 5A, 7, 8:
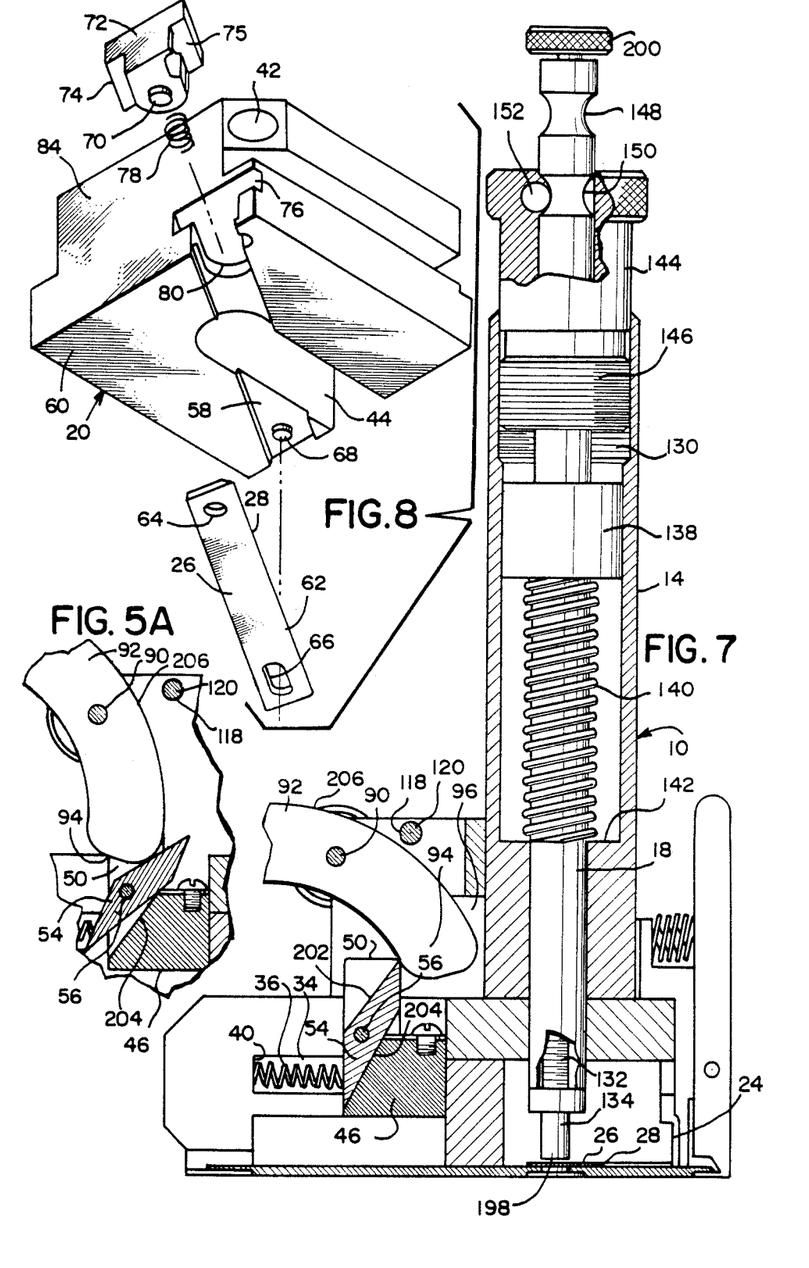
FIG. 5a is a partial, cross sectional view showing the pivotal movement of the detent to permit pivotal movement of the operating lever toe form its fired position to its cocking position.
FIG. 7 is a cross sectional view taken along line 7—7 on FIG. 6, looking in the direction of the arrows, and partly broken away to show interior construction details.
FIG. 8 is an enlarged, exploded, perspective view of the crosshead.
Figure 6:
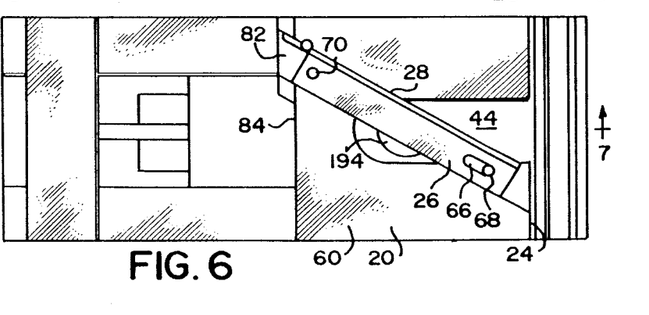
FIG. 6 is bottom plan view of the dermatome, looking from line 6—6 on FIG. 5.

A heavy metal crosshead 20 is reciprocal at the bottom of the base 12 between an initial or cocked position 22 as illustrated in FIGS. 1, 3 and 4 to a final or fired position 24 as shown in FIGS. 5, 6, and 7. As illustrated in FIGS. 4 and 6, a razor or other type of blade 26 is bottomly affixed to the crosshead 20 and is carried by the crosshead from an initial position which is longitudinally juxtaposed to the plunger 18 to a final position wherein the cutting edge 28 of the blade 26 is carried past the plunger. See FIGS. 5 and 6.

As best seen in FIG. 2, the crosshead 20 comprises generally left and right flanges 30, 32 to ride in respective tracks 34 which are provided in the base 12, thereby defining horizontal reciprocal movement of the crosshead 20 relative to the base 12. A pair of crosshead coil springs 36, 38 are respectively positioned within the tracks 34 and bias between the track rearward walls 40 (FIG. 5) and the crosshead recesses 42 (FIG. 2) to continuously urge the crosshead 20 toward its final position 24. When the crosshead 20 is initially moved to the cocked position 22 as shown in FIGS. 1 and 3, the crosshead springs 36, 38 will be compressed to provide the required energy that is necessary to rapidly propel the crosshead 20 from left to right as viewed in FIGS. 3 and 5 when the device is fired.

Still referring to FIG. 2 and as additionally shown in FIGS. 2 and 5, the crosshead is fabricated of generally U-shaped configuration to define a central slot 44 to allow crosshead movement about and longitudinally beyond the plunger 18. A firing block 46 is rearwardly secured to the crosshead 20 by suitable bolts 48, 49 and includes a pair of spaced, vertical fingers 50, 51 which define a detent operating space 52 therebetween. The detent 54 is pivotal about a pin 56 within the operating space 52 for cocking and releasing the crosshead 20 in the manner hereinafter set forth.

Referring now to FIGS. 4, 6 and 8, a straight razor or other blade 26 is bottomly secured to the crosshead 20 within an angularly positioned recess 58 for skin severing purposes as the crosshead is propelled from its cocked position 22 to its final position 24. Preferably, the depth of the angular recess 58 is substantially equal to the thickness of the blade 26 so that the blade will be flush with the bottom 60 of the crosshead 20 when properly installed. As shown, the razor 26 comprises generally a flat body 62 having a cutting surface 28 provided along the leading longitudinal edge of the blade. A pair of endwardly positioned openings 64, 66 are provided through the blade body to mount the blade 26 in a secure manner. One of the openings 66 may be elongated in known manner to facilitate the application of the blade to the crosshead. As best seen in FIG. 8, the crosshead bottom recess 58 is provided with a fixed pin 68 and an adjustable pin 70 for blade securing purposes. Preferably, the blade securing pins 68, 70 are outwardly undercut beneath their respective bottom termini to receive and secure thereunder the endward edges of the blade openings 64, 66 to thereby positively discourage any tendency of the blade 26 to unitentionally become disassociated from the crosshead.

As shown in FIG. 8, and adjusting block 72 includes left and right flanges 74, 75 of size and configuration to slide within cooperating tracks 76 in the angular opening which is formed in one bottom corner of the crosshead 20. The movable or adjustable pin 70 is mounted in the block 72 to thereby be axially movable along the blade recess 58 when the block itself is moved. A coil spring 78 biases between the inward end of the adjusting block 72 and the base of the angular opening to continuously bias the block 72 angularly outwardly of the crosshead 20. The rectangular opening communicates with a block opening 80, which opening is in longitudinal alignment with the blade recess 58. Accordingly, the adjusting block 72 is longitudinally movable into and out of the recess 58 for blade mounting and blade securing purposes.

As shown in FIGS. 1, 4 and 6, under bias of the spring 78, the rearward portion 82 the adjusting block 72 extends rearwardly of the crosshead 20 to provide convenient access for either installing or removing a blade 28. By pushing the rearward portion 82 toward the crosshead 20 to position wherein the rearward edge of the block 72 aligns with the rearward edge 84 of the crosshead 20, the spring 70 will be depressed and the adjustable pin 70 will be urged towards the fixed pin 68 to thereby facilitate insertion or removal of the blade 28 at the elongated blade opening 66. As above set forth, the undercut of the pins 68, 70 will positively secure the blade 26 inasmuch as the bias of the spring 78 will function to assure that the parts cannot unintentionally be separated.

Referring now to FIGS. 1 and 2, a generally J-shaped operating lever 86 is operatively secured to its mounting yolk 88 through a pivot pin 90. The lever 86 comprises a handle portion 92 which integrally connects to engaging portion or toe 94 and defines a rounded pin contacting surface 206 for safety catch purposes, as hereinafter more fully explained.

As illustrated in FIG. 2, a safety block 96 is secured to the top of the base 12 by a conventional machine bolt 98 and is drilled or otherwise machined to provide a transverse opening 100 through which an arming pin 102 is movable. A spring 104 biases between a shoulder 106 on the pin 102 and a portion of the safety block 96 in a manner to continuously urge the pin 102 to a position forwardly of the lever 86 to be engaged by the lever forward surface 206. Upon pulling the attached knob 108 to the left as shown in FIG. 2, the pin 102 can be pulled against the bias of the spring 104 to a position that will be transversely clear of the plane of travel of the lever engaging portion 94. The yolk 88 includes a pin opening 110 to receive the end of the pin 102 after the mechanism has been fired. In this way, the arming pin 102 will function to obstruct movement of the operating lever 86 after firing to thereby prevent unintentional cocking or loading of the device in a manner to prevent injury to an unsuspecting person. In order to arm the dermatome of the present invention, it is first necessary to consciously pull the knob 108 to urge the arming pin 102 to the left as viewed in FIG. 2 by overcoming the bias of the coil spring 104. Once the pin 102 has been pulled to the left, the operating lever will be free to be rotated about its pivot pin 90 for rearing the dermatome in the manner hereinafter more fully set forth.

The yolk 88 may conventionally be secured to the barrel 14 by employing at least two machine bolts 112, 112 which respectively are positioned through yolk openings 114, and into threaded barrel openings 116. The yolk additionally is provided with a transverse opening 118 within which a shouldered safety pin 120 is transversely moveable. The safety pin 120 comprises a relatively large diameter cylindrical shoulder 122 which is normally biased by a spring 124 to a position immediately in front of the forward surface 206 of the operating lever 86 to prevent unintentional firing of the device. By pushing on the end knob 126, the coil spring 124 can be compressed and the cylindrical shoulder 122 will be urged laterally out of the path of travel of the lever 86. The elongated pin section 128 is formed of diameter small enough to permit sufficient pivotal movement of the operating lever 86 to allow the engaging portion 94 of the lever 86 to clear the detent 54 to fire the device. Thus it is seen that conscious movement of the arming pin 102 must be made before the dermatome can be loaded and an additional conscious, transverse movement of the safety pin 120 must be made before the device can be fired.

Referring now to FIG. 2 and to FIG. 7, it will be seen that the barrel or stem 14 is generally hollow and is provided with an upper, interior thread 130 to threadedly and adjustably receive the plunger assembly 16 therewithin. The plunger assembly 16 comprises an elongated rod or plunger 18 which terminates downwardly in a threaded recess 132, which recess is designed to accommodate any one of a number of readily interchangeable, differently sized plunger pins 134. AS hereinafter more fully set forth, the operating shank 136 of a plunger pin may thereby be interchanged so as to vary the diameter and configuration of the plunger pin shank whenever necessary. In this manner, by varying the size and configuration of the plunger pin shank (and its associated bottom plate opening 192) the size and shape of the wound produced by the dermatome 10 can be readily varied.

The plunger assembly 16 further comprises a stabilizing, cylindrical shoulder 138 of diameter to snuggly fit within the interior periphery of the dermatome barrel 14 in a manner to permit longitudinal reciprocation of the plunger 18 within the stem 14. A sturdy coil spring 140 biases between the bottom of the shoulder 138 of the plunger and an interior ledge 142 which is bottomly formed in the stem 14 for precise height adjustment and operating purposes. The plunger 18 is vertically reciprocal through an axial opening 143 which is provided through the upper securing member 144 between its lower, skin adhering position (FIG. 5) to its upper, skin cutting position (FIG. 3). The securing member 144 comprises a lower threaded section 146 which is in adjustable, threaded engagement with the upper stem threaded section 130. It will be seen that when the securing member threaded section 146 is engaged with the threaded section 130 of the stem 14, the plunger assembly 16 will be adjustably locked in position for skin attracting purposes as hereinafter more fully set forth.

Still referring to FIG. 2 and to FIG. 7, the upper end of the plunger 18 is undercut in known manner to provide a pair of vertically spaced upper and lower grooves 148, 150 for plunger height securing purposes. The securing member 144 is upperly provided with an axially offset, horizontal opening 160 through which is positioned a plunger securing pin 152 in a manner to allow horizontal reciprocal motion therewithin. The securing pin 152 comprises end threads 158 and an interiorly threaded end cap 156, which cap is removable to facilitate assembly. A second end cap 162 secures at the opposite end of the pin 152 to prevent disassociation of the parts. The pin 152 is provided with an undercut area 154 of size to permit passage of the outer periphery of the plunger 18. Accordingly, when the plunger 18 is to be vertically moved within the stem 14, the undercut area of the pin 152 should be pushed into alignment with the outer periphery of the plunger to thus allow vertical movement.

When it is desired to lock the plunger in its upper position as illustrated in FIGS. 3 and 7, after the plunger has been properly positioned by pressing the cap 200 to compress the coil spring 140, the pin 152 may be horizontally moved within the opening 160 to engange the lower peripheral groove 150 in the manner illustrated. Whenever necessary to lock the plunger in its lower (FIG. 5) position, the pin 152 may be horizontally moved as necessary to align the undercut area 154 with the outer periphery of the plunger. When the upper groove 148 of the plunger 18 is pushed into alignment with the pin 152 by compressing the spring 140, horizontal movement of the pin within the opening 162 will thereby lock the plunger against the bias of the spring 140 in its lower position. The relative upper and lower positions of the plunger 18 may be adjusted by threadedly turning the threaded section 146 within the barrel threads 130 to reach the desired vertically adjusted positions. As shown in FIG. 1, a suitable scale 164 may be applied to the outer periphery of the securing member 144 to precisely adjust the vertical position of the plunger pin 134. In the preferred embodiment, the micrometer adjustment is designed so that one revolution of the member 144 will be equal to one millimeter of height adjustment. An index 166 provided on the top of the barrel 14 can be provided in known manner to facilitate the scale reading and precise duplication of the depth of cut. It will be appreciated that when the plunger is raised so that its plunger pin is raised within the dermatome, more skin will be pulled upwardly through the plate opening 192 and hence, upon operation, the dermatome will cut a deeper wound.

A bottom plate 168 removeably secures to the bottom of the base 12 and serves both to assist in precisely defining the area of skin to be cut and additionally performs a safety function in covering the blade 26 both when it is at rest and when it is in movement. The plate 168 includes front and rear, thin, end flanges 170, 172 for securing the plate in position. A rear plate securing member 174 is bottomly affixed to the base 12 in a manner to define a transverse recess of sufficient depth to receive the rear flange 172 of the bottom plate 168 therein in a secure but removeable manner. At the front of the base 12 is mounted a plate securing assembly 176 which is secured to the front of the base 12 in known manner, for example by employing a pair of machine bolts 178, 179.

The plate securing assembly comprises generally a machined body 180 having a vertically open recess 182 therein. A plate securing a lever 184 is pivotal within the recess 182 about a pivot pin 186 to urge the bottom gripper 188 into and out of engagement with the front plate flange 170. A coil spring 190 is positioned within an upper portion of the recess 182 and normally biases the lever 184 about the pin 186 to continuously engage the bottom gripper 188 with the front bottom plate flange 170. In order to remove the bottom plate 168 when desired for the wound size adjustment as hereinafter set forth, the lever 184 should be pivoted about the pin 186 to depress the spring 190 sufficiently to release the bottom gripper 188 from engagement with the bottom plate front flange 170. The bottom plate includes a precisely sized opening 192 of size and position to receive the shank 136 of a plunger pin 134 therethrough. The bottom surface of the plate is machined or otherwise treated to provide a concentric recess 194 about the plunger pin opening 192. As above set forth, the concentric recess acts in conjunction with the natural elasticity and resiliency of the skin to facilitate drawing the skin 196 up for displacement through the plate opening 192 in the manner illustrated in FIG. 3. If desired, the plate opening 192 could be enlarged as required to permit removal of larger pathological skin conditions, such as warts.

In order to use the dermatome of the present invention for securing a plurality of precisely sized specimens or for forming a plurality of precisely sized, similarly shaped wounds, a plunger pin 134 having an operating shank 136 of the desired size and configuration is selected and the pin threads 130 are engaged upon the threaded recess 132 of the plunger 18 is usual manner. A cooperating bottom plate 168 with a properly sized plate opening 192 is applied to the bottom of the base 12 upon proper manipulation of the plate securing assembly 176. With the proper sized plunger pin in position, a suitable adhesive (not shown) (such as "Crazy Glue") or perhaps vacuum (not shown) is applied over the bottom surface 198 of the operating shank 136 and the plunger cap 200 is pressed to extend the shank 136 through the plate opening 192 until the shank bottom 198 contacts the skin 196. Release of pressure upon the plunger cap 200 will allow the coil spring 140 to bias the plunger assembly upwardly.

The specimen of skin which is adhered to the bottom of the shank 136 will then be pulled upwardly through the plate opening 192 and will remain in the position illustrated in FIG. 3. In FIG. 3 it will be noted that the engaging toe 94 of the operating lever 96 is engaged upon the upwardly extending portion of the detent 54 to thereby maintain the crosshead 20 in its cocked position 22. When the toe 94 is pivoted upwardly clear of the dentent 54 by squeezing the lever handle portion 92, the crosshead springs 36, 38 cause the crosshead to rapidly travel from left to right, as illustrated in FIGS. 3 and 5 whereby the cutting edge 78 of the blade 26 will traverse below the plunger pin shank 136 to sever a predetermined, particularly configured speciment of skin. The rapidity of movement of the crosshead from the cocked position 22 to the final position 24, in combination with the weight and momentum of the crosshead, will cause the skin to be severed without any conscious feeling or pain on the part of the patient.

After the crosshead 20 has been released to its final or fired position 24, as seen in FIG. 5, it will be noted that the engaging portion or toe 94 of the operating lever 86 will be entirely clear of the pivotal detent 54. In this position, as above set forth, the arming pin 102 will have been urged by its associated spring 104 to enter the yolk opening 110, thereby preventing counterclockwise rotation of the lever 86 about the pivot pin 90. Upon pulling the arming pin knob 108 transversely to overcome the bias of the spring 104, the pin 102 will be pulled out of contact with the operating lever 86, thereby freeing the engaging toe 94 to travel over the upper surface 202 the detent 54 from left to right as viewed in FIG. 7. The contact of the toe 94 with the upper surface 202 will cause clockwise rotation of the detent 54 about its pivot pin 56. This notation lowers the dentent sufficiently to enable the toe 94 to pass over the detent.

Once the toe has passed, the geometry of the detent 54 and the weight of its lower portion will cause it to assume its original position of generally a forty-five degree angularity as shown by rotating in a counterclockwise direction about its pivot pin 56. In this position, the lower surface 204 of the detent 54 will engage and lock upon the lower portion of the block 46 at the operating space 52 thereof to prevent further counterclocwise movement about the pin 56, thereby locking the toe 94 forwardly of the detent 54. See FIG. 7. Then upon clockwise rotation of the lever 86 about its pivot 90 (after pulling the arming pin knob 108), the toe 94 (which is engaged upon the pivotal detent 54) will cause the crosshead to be urged rearwardly against the bias of the crosshead springs 36, 38 to the position illustrated in FIGS. 1 and 3. In this position, the thick shoulder 122 of the safety pin 120 will be positioned immediately forwardly of the front surface 206 of the operating lever 86 to thereby prevent any further unintentional clockwise rotation of the lever about its pivot 90.

In order to fire the mechanism, it is first necessary to push the end knob 126 of the safety pin 120 against the bias of the spring 124 to thereby position the thinner pin section 128 immediately in front of the lever forward surface 206. The difference in diameter between the pin section 128 and the thick shoulder 122 is just sufficient to allow a slight additional pivotal rotation of the lever 86 for crosshead firing purposes. While pushing the safety pin knob 126, the lever handle portion 92 can be squeezed to further rotate the lever 86 in a clockwise rotation sufficiently to allow the lever engaging portion 94 to ride over and clear of the top of the detent 54, this additional rotation then permits the crosshead springs 36, 38 to rapidly propel the crosshead from the cocked position 22 as shown in FIGS. 1 and 3 to the final or fired position 24 as illustrated in FIGS. 5 and 7. Thus it is seen that two conscious efforts must be made in order to fire the device, first pulling the arming pin 102 and then pressing the safety pin 120, thereby preventing accidental loading and discharge and possible accidental injury.

By repeating the steps of placing an adhesive on the bottom 198 of the plunger pin 136, lowering the plunger pin shank 136 through the plate opening 192 to adhere to a section of skin 196, raising the plunger 18 and pulling a portion of the skin through the bottom plate opening, cocking the dermatome to pull the crosshead 30 to its initial position 22 and then simultaneously pressing the shouldered safety pin knob 126 while squeezing the handle portion 92 operating lever 86, crosshead will be released to rapidly traverse and thus sever another specimen of skin.

Although the invention has been described with a certain degree of particularity, it is understood that the present disclosure has been made only by way of example and that numerous change in the details of construction and the combination and arrangement of parts may be resorted to without departing the spirit and scope of the invention.

What is claimed is:

1. The method of cutting specimens of skin with dermatome of the type comprising a body, a blade containing crosshead horizontally reciprocal within the body, a bottom plate bottomly covering the crosshead and the blade, the bottom plate having an opening and a plunger assembly including a bottom plunger pin vertically movable relative to the body comprising
    lowering the plunger assembly and projecting the bottom plunger pin through the bottom plate the opening and below the bottom plate;
    equipping the bottom of the plunger pin with a skin attracting media;
    contacting the sking below the bottom plate with the plunger pin and adhering the skin to the plunger pin;
    raising the plunger assembly and drawing the skin upwardly through the bottom plate opening and above the bottom plate; and
    horizontally moving the crosshead above the bottom plate and severing the skin with the blade above the bottom plate.

2. The method of claim 1 wherein the equipping comprises applying an adhesive to the bottom of the plunger pin prior to contacting.

3. The method of claim 1 wherein the drawings comprises stretching the skin.

4. The method of claim 1 wherein the moving comprises spring biasing the crosshead rapidly across the body.

* * * * *

UNITED STATES PATENT AND TRADEMARK OFFICE
CERTIFICATE OF CORRECTION

PATENT NO. : 4,838,284

DATED : June 13, 1989

INVENTOR(S) : Morris V. Shelanski

It is certified that error appears in the above-identified patent and that said Letters Patent is hereby corrected as shown below:

In Column 1, line 21, change "emplot" to --employ--.

In Column 1, line 66, change "ajustable" to --adjustable--.

In Column 4, line 16, change "form" to --from--.

In Column 4, line 40, change "pluger" to --plunger--.

Signed and Sealed this

Tenth Day of April, 1990

Attest:

HARRY F. MANBECK, JR.

*Attesting Officer*  *Commissioner of Patents and Trademarks*